(12) United States Patent
Zhang et al.

(10) Patent No.: US 9,114,179 B2
(45) Date of Patent: *Aug. 25, 2015

(54) IMMUNOCONJUGATE FORMULATIONS

(75) Inventors: Wei Zhang, Philadelphia, PA (US);
Michael S. Fleming, Londonderry, NH (US); Godfrey Amphlett, Cambridge, MA (US); Hung-wei Chih, Burlingame, CA (US); Elizabeth Bartlett, Cambridge, MA (US)

(73) Assignee: ImmunoGen, Inc., Waltham, MA (US)

( * ) Notice: Subject to any disclaimer, the term of this patent is extended or adjusted under 35 U.S.C. 154(b) by 206 days.

This patent is subject to a terminal disclaimer.

(21) Appl. No.: 11/498,139

(22) Filed: Aug. 3, 2006

(65) Prior Publication Data

US 2007/0031402 A1    Feb. 8, 2007

Related U.S. Application Data

(60) Provisional application No. 60/704,902, filed on Aug. 3, 2005, provisional application No. 60/707,162, filed on Aug. 11, 2005, provisional application No. 60/746,454, filed on May 4, 2006, provisional application No. 60/746,456, filed on May 4, 2006.

(51) Int. Cl.
| | |
|---|---|
| *A61K 39/395* | (2006.01) |
| *A61K 47/48* | (2006.01) |
| *A61K 9/00* | (2006.01) |
| *A61K 47/10* | (2006.01) |
| *A61K 47/26* | (2006.01) |
| *A61K 47/40* | (2006.01) |

(52) U.S. Cl.
CPC ......... *A61K 47/48561* (2013.01); *A61K 9/0019* (2013.01); *A61K 47/48384* (2013.01); *A61K 47/48615* (2013.01); *A61K 47/10* (2013.01); *A61K 47/26* (2013.01); *A61K 47/40* (2013.01)

(58) Field of Classification Search
None
See application file for complete search history.

(56) References Cited

U.S. PATENT DOCUMENTS

| | | | |
|---|---|---|---|
| 3,890,238 A * | 6/1975 | Boehmer ..................... 252/1 | |
| 3,896,111 A | 7/1975 | Kupchan et al. | |
| 4,151,042 A | 4/1979 | Higashide et al. | |
| 4,563,304 A | 1/1986 | Carlsson et al. | |
| 4,597,966 A * | 7/1986 | Zolton et al. ................ 424/141.1 | |
| 5,196,193 A | 3/1993 | Carroll | |
| 5,208,020 A | 5/1993 | Chari et al. | |
| 5,225,539 A | 7/1993 | Winter | |
| 5,416,064 A | 5/1995 | Chari et al. | |
| 5,475,092 A | 12/1995 | Chari et al. | |
| 5,545,806 A | 8/1996 | Lonberg et al. | |
| 5,569,825 A | 10/1996 | Lonberg et al. | |
| 5,585,089 A | 12/1996 | Queen et al. | |
| 5,639,641 A | 6/1997 | Pedersen et al. | |
| 5,665,357 A | 9/1997 | Rose et al. | |
| 5,693,761 A | 12/1997 | Queen et al. | |
| 5,714,352 A | 2/1998 | Jakobovits | |
| 6,171,586 B1 | 1/2001 | Lam et al. | |
| 6,265,150 B1 | 7/2001 | Terstappen et al. | |
| 6,267,958 B1 * | 7/2001 | Andya et al. ............... 424/130.1 | |
| 6,333,410 B1 | 12/2001 | Chari et al. | |
| 6,340,701 B1 | 1/2002 | Chari et al. | |
| 6,372,738 B2 | 4/2002 | Chari et al. | |
| 6,436,931 B1 | 8/2002 | Chari et al. | |
| 6,441,163 B1 | 8/2002 | Chari et al. | |
| 6,716,821 B2 | 4/2004 | Zhao et al. | |
| 6,756,397 B2 | 6/2004 | Zhao et al. | |
| 6,824,780 B1 | 11/2004 | Devaux et al. | |
| 7,097,840 B2 | 8/2006 | Erickson et al. | |
| 7,374,762 B2 * | 5/2008 | Amphlett et al. .......... 424/184.1 | |
| 7,494,649 B2 * | 2/2009 | Amphlett et al. .......... 424/133.1 | |
| 7,501,120 B2 * | 3/2009 | Amphlett et al. .......... 424/133.1 | |
| 7,514,080 B2 * | 4/2009 | Amphlett et al. .......... 424/133.1 | |
| 8,012,485 B2 | 9/2011 | Amphlett et al. | |
| 2001/0036923 A1 | 11/2001 | Chari et al. | |
| 2002/0001587 A1 | 1/2002 | Erickson et al. | |
| 2002/0028178 A1 | 3/2002 | Hanna et al. | |

(Continued)

FOREIGN PATENT DOCUMENTS

| | | |
|---|---|---|
| CA | 2387108 A1 | 6/2001 |
| EP | 0 239 400 B1 | 8/1994 |

(Continued)

OTHER PUBLICATIONS

Tassone et al. Cancer Research, vol. 64, p. 4629-4636, 2004.*
Harris, R.J, et al., "Commercial Manufacturing Scale Formulation and Analytical Characterization of Therapeutic Recombinant Antibodies", Drug Development Research, vol. 61, No. 3, pp. 137-154 Mar. 1, 2004.
International Search Report dated Feb. 7, 2011, as issued in European Patent Application No. 06800717.8.
International Search Report dated Mar. 30, 2007, as issued in International Application No. PCT/US06/30295.

(Continued)

*Primary Examiner* — Yunsoo Kim
(74) *Attorney, Agent, or Firm* — Leydig, Voit & Mayer, Ltd.

(57) ABSTRACT

The present invention provides an immunoconjugate formulation that is substantially free of particles, the immunoconjugate formulation comprising: an immunoconjugate and one or more excipients selected from the group consisting of: sucrose, polysorbate 20, polysorbate 80, cyclodextrin, dextrose, glycerol, polyethylene glycol, mannitol, sodium chloride, and an amino acid, wherein the formulation is a buffered aqueous solution having a pH of 4.5 to 7.6. The present invention also provides an immunoconjugate formulation that is substantially free of aggregates, the immunoconjugate formulation comprising: an immunoconjugate and one or more excipients selected from the group consisting of histidine, sucrose, glycine and sodium chloride, wherein the formulation is a buffered aqueous solution having a pH of 4.5 to 7.6. The present invention further provides an immunoconjugate formulation that is substantially free of both particles and aggregates.

52 Claims, No Drawings

(56) References Cited

U.S. PATENT DOCUMENTS

| | | | |
|---|---|---|---|
| 2002/0028515 | A1 | 3/2002 | Talmadge et al. |
| 2002/0041847 | A1 | 4/2002 | Goldenberg |
| 2002/0197266 | A1 | 12/2002 | Debinski |
| 2003/0004210 | A1 | 1/2003 | Chari et al. |
| 2004/0126379 | A1* | 7/2004 | Adolf et al. ............... 424/178.1 |
| 2004/0241174 | A1 | 12/2004 | Amphlett et al. |
| 2004/0247588 | A1 | 12/2004 | Johnson et al. |

FOREIGN PATENT DOCUMENTS

| | | |
|---|---|---|
| EP | 1 314 437 A1 | 5/2003 |
| GB | 2 188 638 A | 10/1987 |
| JP | 2004-538287 A | 12/2004 |
| JP | 2005-508981 A | 4/2005 |
| WO | 97/04801 A1 | 2/1997 |
| WO | WO 98/56418 * | 12/1998 |
| WO | WO 00/02587 A1 | 1/2000 |
| WO | 01/00244 | 1/2001 |
| WO | 01/21763 | 4/2001 |
| WO | WO 01/24763 A2 | 4/2001 |
| WO | WO 01/38318 A1 | 5/2001 |
| WO | WO 01/40309 A2 | 6/2001 |
| WO | WO 01/49698 A1 | 7/2001 |
| WO | WO 02/13860 A1 | 2/2002 |
| WO | WO 02/16401 A2 | 2/2002 |
| WO | WO 02/060955 A2 | 8/2002 |
| WO | WO 02/092127 A1 | 11/2002 |
| WO | WO 03/009817 A3 | 2/2003 |
| WO | 03/039485 A2 | 5/2003 |
| WO | WO 03/057163 A2 | 7/2003 |
| WO | WO 03/097625 A1 | 11/2003 |
| WO | 03/105894 A1 | 12/2003 |
| WO | 04/001007 A2 | 12/2003 |
| WO | 2004/004639 A2 | 1/2004 |
| WO | 2004/018000 A2 | 3/2004 |
| WO | WO 2004/060343 A1 | 7/2004 |
| WO | WO 2004/066957 A2 | 8/2004 |
| WO | 2004/110498 | 12/2004 |
| WO | WO 2005/014862 A1 | 2/2005 |
| WO | WO 2005/065709 A2 | 7/2005 |
| WO | WO 2005/065717 A2 | 7/2005 |

OTHER PUBLICATIONS

Arakawa et al., Biophysical Journal, 47: 411-414 (1985).
Baeckstrom et al., *The Journal of Biological Chemistry*, 266(32): 21537-21547 (Nov. 15, 1991).
Bartnes, *Tidsskr. Nor. Laegforen.*, 121, 2941-2945 (2001).
Behm et al., *Blood*, 87, 1134-1139 (1996).
Carlsson et al., *Biochemical Journal*, 173, 723-737 (1978).
Chang et al., *Cancer Res.* 59, 3192-3198 (1999).
Colomer et al., *Cancer Investigation*, 19 (1), 49-56 (2001).
Davis et al., *Nature Reviews. Drug Discovery*, 3: 1023-1035 (2004).
Francisco et al., *Blood*, 102 (4), 1458-1465 (2003).
Ghetie et al., *Journal of Immunological Methods*, 112, 267-277 (1988).
Groves et al., Aseptic Pharmaceutical Manufacturing II: Applications for the 1990s, pp. 291-309 (1995).
Haskard et al., *J. Immunol. Methods*, 74(2), 361-367 (1984).
Heider et al., *European Journal of Cancer*, 31A (13/14), 2385-2391 (1995).
Huse et al., *Science*, 246, 1275-1281 (1989).
Ichimura et al., *Journal of Antibiotics*, 44 (10), 1045-1053 (1991).
Kearse et al., *Int. J. Cancer*, 88, 866-872 (2000).
Kohler et al., *Eur. J. Immunol.*, 5, 511-519 (1976).
Kupchan et al., *Journal of Medicinal Chemistry*, 21 (1), 31-37 (1978).
Lee et al., *The Journal of Biological Chemistry*, 256(14): 7193-7201 (1981).
Lepage et al., *American Assn. for Cancer Research (AACR), 2003 Annual Meeting*, Poster Abstract 749.
Liu et al., *Proc. Natl. Acad. Sci*, 93, 8618-8623 (1996).
Maloney et al., *Blood*, 90 (6), 2188-2195 (1997).
Manning et al., *Pharmaceutical Research*, 6(11): 903-918 (1989).
Miotti et al., *Int. J. Cancer*, 39, 297-303 (1987).
Nadler et al., *Journal of Immunology*, 131 (1), 244-250 (1983).
Pedersen et al., *Journal of Molecular Biology*, 235 (3), 959-973 (1994).
Reiter et al., *Protein Engineering*, 7 (5), 697-704 (1994).
Remillard et al., *Science*, 189 (4207), 1002-1005 (1975).
Roder et al., *Methods Enzymol.*, 121, 140-167 (1986).
Roguska et al., *Proc. Natl. Acad. Sci.*, 91, 969-973 (1994).
Roguska et al., *Protein Engineering*, 9(10): 895-904 (1996).
Sasse et al., *Journal of Antibiotics*, 53 (9), 879-885 (2000).
Suzawa et al., *Bioorganic and Medicinal Chemistry*, 8, 2175-2184 (2000).
Von Mensdorff-Pouilly et al., *Int. J. Biol. Markers*, 15, 343-356 (2000).
Wang et al., Stability and Characterization of Protein and Peptide Drugs: Case Histories, pp. 263-286 (1993).
Wang, *International Journal of Pharmaceutics*, 203, 1-60 (2000).
Welt et al., *Journal of Clinical Oncology*, 12 (6), 1193-1203 (1994).
Yoshitake et al., *European Journal of Biochemistry*, 101, 395-399 (1979).
Yu et al., *Investigative Ophthalmology & Visual Science*, 49(2): 522-527 (2008).
Extended European Search Report issued in European Patent Application No. 10011901.5, dated Dec. 27, 2011.
International Search Report and Written Opinion issued in International Patent Application No. PCT/US2004/015376, mailed on Jun. 16, 2005.
International Preliminary Report on Patentability (Chapter II) issued in International Patent Application No. PCT/US2004/015376, dated Nov. 28, 2005.
Jiang et al., *J. Biol. Chem.*, 280(6) 4656-4662 (2005).
MacCallum et al., *J. Mol. Biol.*, 262: 732-745 (1996).
Wu et al., *J. Mol. Biol.*, 294: 151-162 (1999).

* cited by examiner

IMMUNOCONJUGATE FORMULATIONS

This application claims benefit under 35 U.S.C. §119(e) to Application Nos. 60/704,902 filed Aug. 3, 2005; 60/707,162 filed Aug. 11, 2005; 60/746,454 filed May 4, 2006; and 60/746,456 filed May 4, 2006, the disclosures of which are each hereby incorporated by reference in their entireties.

FIELD OF THE INVENTION

The present invention relates to methods for the preparation of stable formulations of immunoconjugates, which are pharmaceutical compounds that are composed of an antibody and one or several covalently linked molecules of a drug.

BACKGROUND OF THE INVENTION

Immunoconjugates are developed as highly potent and specific agents for the treatment of cancer and other conditions. An immunoconjugate is composed of an antibody specifically recognizing a target cell antigen, such as a tumor cell antigen, and one or several covalently linked molecules of a drug, particularly a cytotoxic drug such as a maytansinoid, a taxane, or a CC-1065 analog. Another name used for such immunoconjugates is antibody-drug conjugates. Immunoconjugates are inactive during circulation but bind to target cell surfaces, whereupon they are internalized by the cells. By mechanisms not yet fully understood, the drugs are subsequently released from the antibody and can exert their pharmacological effect.

The targeted delivery of cytotoxic drugs to target cells, such as cells making up cancer tissue, potentially improves the therapeutic indexes of the cytotoxic drugs. Typically, cytotoxic drugs used as immunoconjugates are 100 to 1000-fold more potent than conventional chemotherapy drugs. Examples of such immunoconjugates are disclosed in International (PCT) Patent Application Nos. WO 00/02587, 02/060955, and 02/092127; U.S. Pat. Nos. 5,475,092, 6,340,701, 6,171,586, 6,706,708 B2, and 6,756,397 B2; and Chari et al., *Cancer Res.*, 52, 127-131 (1992).

Pharmaceutical compounds such as immunoconjugates are generally combined with one or more pharmaceutically acceptable carriers, excipients, and/or stabilizers to provide a pharmaceutical composition that allows for administration to patients and for storage and transport of the pharmaceutical compound. Like other protein pharmaceuticals, immunoconjugates are prone to degradation such as oxidation, deamidation, as well as particle and aggregate formation, etc. (Manning et al., *Pharm. Res.* 6, 903-918 (1989); Ahern and Manning, *Stability of Protein Pharmaceuticals: Part A, Chemical and Physical pathways of Protein Degradation*, Plenum, New York, (1992); and Cleland et al., *Crit. Rev. Ther. Drug Carrier Syst.* 10, 307-377 (1993)).

Particle formation in protein pharmaceuticals, in particular, can destabilize the pharmaceutical compound, thus making the formulation less potent or even harmful for clinical use. For example, particles in injected pharmaceutical formulations can cause significant injury to veins or prolonged venous stasis in patients. In addition, aggregate formation is a major degradation pathway of protein pharmaceuticals (Chari et al., *Pharm Res.* 20, 1325-1336 (2003)), and may lead to undesirable effects such as immunogenicity.

The conjugation of drugs, especially cytotoxic drugs, which are often hydrophobic, small molecules, to hydrophilic monoclonal antibodies, introduces additional instability to immunoconjugates. Addressing the properties attributable to the antibody component of immunoconjugates is critical to the generation of stable liquid or lyophilized pharmaceutical formulations. To this end, WO 2004/004639 A2 and U.S. Patent Application No. 2004/0,241,174 A1 describe compositions of immunoconjugates. However, these compositions do not adequately address particle and aggregate formation in pharmaceutical compositions of immunoconjugates.

Thus, there remains a need for pharmaceutical compositions of immunoconjugates that are substantially free of particles and/or aggregates, and remain substantially free of particles and/or aggregates during storage and transport.

The present invention provides pharmaceutical compositions of immunoconjugates that are substantially free of particles and/or aggregates and prevent the formation of particles and/or aggregates during storage and/or transport. Methods for use of the pharmaceutical compositions are also provided. These and other advantages of the invention, as well as additional inventive features, will be apparent from the description of the invention provided herein.

BRIEF SUMMARY OF THE INVENTION

The present invention is based on the finding that particle and aggregate formation in pharmaceutical compositions of immunoconjugates can be inhibited by using certain excipients. The novel formulations yield greater stability and substantially longer shelf lives for the pharmaceutical compounds and provide assurance of patient safety.

One aspect of the present invention provides an immunoconjugate formulation that is substantially free of particles, the immunoconjugate formulation comprising: an immunoconjugate and one or more excipients selected from the group consisting of: sucrose, polysorbate 20, polysorbate 80, cyclodextrin, dextrose, glycerol, polyethylene glycol, mannitol, sodium chloride, and an amino acid, wherein the formulation is a buffered aqueous solution having a pH of 4.5 to 7.6.

A second aspect of the present invention provides an immunoconjugate formulation that is substantially free of aggregates, the immunoconjugate formulation comprising: an immunoconjugate and one or more excipients selected from the group consisting of histidine, sucrose, glycine and sodium chloride, wherein the formulation is a buffered aqueous solution having a pH of 4.5 to 7.6.

The present invention further provides an immunoconjugate formulation that is substantially free of both particles and aggregates.

DETAILED DESCRIPTION OF THE INVENTION

The present invention provides stable pharmaceutical compositions of immunoconjugates that are substantially free of particles and/or aggregates and remain substantially free of particles and/or aggregates over a prolonged period of storage and during transport. The present invention is based on the finding that particle and/or aggregate formation in pharmaceutical compositions of immunoconjugates can be inhibited by using certain excipients. The novel formulations yield greater stability and substantially longer shelf lives for the pharmaceutical compounds and provide assurance of patient safety.

Such formulations are prepared by inclusion of an excipient that inhibits or reduces formation of visible (larger than 50 μm) and subvisible (larger than 5 μm) particles. As used herein, a composition that is "substantially free of particles" will pass the US Pharmacopeia (USP) test <788>, which requires that particles with size above 10 μm should be below 6000 counts per container and particles with size above 25 μm should be below 600 counts per container. See USP 28, Chapter 788 "Particulate Matter in Injections," 2004, edited by United States Pharmacopeia, Rockville, Md. As used herein, a composition that is "substantially free of aggregates" will remain free of aggregates during storage and transport so that the immunoconjugate monomer level remains above 95% throughout the shelf life of the composition.

A typical shelf life for the immunoconjugate compositions of the present invention is about 1 to 5 years, preferably 1 to 4 years, more preferably 2 to 4 years, at 4° C.

An immunoconjugate formulation of the invention that is substantially free of particles comprises an immunoconjugate and one or more excipients selected from the group consisting of sucrose, polysorbate 20, polysorbate 80, cyclodextrin, dextrose, glycerol, polyethylene glycol, mannitol, sodium chloride, and an amino acid, wherein the formulation is a buffered aqueous solution having a pH of 4.5 to 7.6. The formulation may comprise one or more excipients selected from the group consisting of: (i) 0.1-12% sucrose, (ii) 0.005-1.0% polysorbate 20, (iii) 0.5-2% beta-cyclodextrin, (iv) 2-8% glycerol, (v) 1-5% PEG6000, (vi) 2-8% mannitol, (vii) 0.005-1.0% polysorbate 80, (viii) 5-20 mM histidine, (ix) 100-300 mM glycine, and (x) 50-300 mM sodium chloride.

In certain preferred embodiments, the formulation of the invention that is substantially free of particles preferably comprises one or more excipients selected from the group consisting of: (i) 5-10% sucrose; (ii) 0.005-0.2% polysorbate 20; (iii) 0.5-1% beta-cyclodextrin; (iv) 2-5% glycerol; (v) 2-3% PEG6000; (vi) 3-5% mannitol; (vii) 0.005-0.2% polysorbate 80; (viii) 10-15 mM histidine; (ix) 130-250 mM glycine, and (x) 100-200 mM sodium chloride.

In preferred embodiments the buffered aqueous solution may contain one or more of histidine, succinate, citrate, phosphate, and acetate, and the pH is preferably from 5.0 to 7.0. The pH of the formulation is more preferably from 5.0 to 6.0.

In certain embodiments of the invention, the immunoconjugate of the formulation comprises a humanized antibody selected from the group consisting of huMy9-6, huC242, huN901, DS6, trastuzumab, bivatuzumab, sibrotuzumab, and rituximab; and/or the immunoconjugate comprises a cytotoxic drug selected from the group consisting of a maytansinoid, a taxane, and a CC-1065. The concentration of immunoconjugate in the inventive formulation can range from between about 0.5 to 20.0 mg per ml. Preferably, the concentration of immunoconjugate is 0.5 to 10 mg per ml.

An immunoconjugate formulation of the invention that is substantially free of aggregates comprises: an immunoconjugate; and one or more excipients selected from the group consisting of histidine, sucrose, glycine and sodium chloride, wherein the formulation is a buffered aqueous solution having a pH of 4.5 to 7.6. Preferably, the immunoconjugate formulation comprises one or more excipients selected from 5-200 mM histidine, 100-200 mM glycine, and 2-8% sucrose.

In certain preferred embodiments, the excipients are 5-100 mM histidine or 100-150 mM glycine, or the formulation contains 2-8% sucrose and 100-150 mM glycine. In certain other preferred embodiments, the formulation contains 10 mM histidine, 5% sucrose and 130 mM glycine.

In preferred embodiments the buffered aqueous solution may contain one or more of histidine, succinate, citrate, phosphate, and acetate, and the pH is preferably from 5.0 to 7.0. The pH of the formulation is more preferably from 5.0 to 6.0.

In another aspect of the invention, the formulation that is substantially free of aggregates further comprises polysorbate 20 and/or polysorbate 80, such that the formulation is also substantially free of particles.

In certain embodiments of the invention, the immunoconjugate of the formulation comprises a humanized antibody selected from the group consisting of huMy9-6, huC242, huN901, DS6, trastuzumab, bivatuzumab, sibrotuzumab, and rituximab; and/or the immunoconjugate comprises a cytotoxic drug selected from the group consisting of a maytansinoid, a taxane, and a CC-1065. The concentration of immunoconjugate in the inventive formulation can range from between about 0.5 to 20.0 mg per ml. Preferably, the concentration of immunoconjugate is 0.5 to 10 mg per ml.

In certain preferred embodiments of the invention, the immunoconjugate formulation is substantially free of both aggregates and particles. For example, the present invention provides an immunoconjugate formulation consisting essentially of: huN901-DM1 immunoconjugate at a concentration of from 0.5-10 mg/ml; 5-15 mM histidine and/or 5-15 mM succinate; 0.1-10% sucrose and/or 100-300 mM glycine; 0.005-0.2% polysorbate 80 and/or 0.005-0.2% polysorbate 20, wherein the formulation is an aqueous buffered solution having a pH of from 5-6. Additional ingredients may be optionally added so long as the formulation remains substantially free of both aggregates and particles.

In another example, an immunoconjugate formulation consists essentially of: (a) huC242-DM4 immunoconjugate at a concentration of from 0.5-10 mg/ml; 5-15 mM histidine; 0.1-10% sucrose and/or 100-300 mM glycine; 0.005-0.2% polysorbate 80 and/or 0.005-0.2% polysorbate 20; wherein the formulation is an aqueous buffered solution having a pH of from 5-6. Additional ingredients may be optionally added, so long as the formulation remains substantially free of both aggregates and particles.

Generally, suitable excipients that may be used in conjunction with the present invention may be selected from a variety of categories, including but not limited to inorganic salts, organic acids, saccharides, amino acids, polysorbates, polyethylene glycol and combinations thereof. Preferred excipients are selected from the group consisting of inorganic salts, organic carboxylic acids, saccharides, amino acids, polysorbates, polyethylene glycol, albumins, glycerol, and combinations thereof.

Examples of suitable inorganic salts include but are not limited to sodium chloride, calcium chloride, magnesium sulphate, magnesium chloride, sodium sulphate, and combinations thereof. Sodium chloride is a preferred excipient for use in the present invention.

Examples of suitable organic carboxylic acids include but are not limited to tartaric acid (which includes racemic tartaric acid, D-tartaric acid and L-tartaric acid) maleic acid, acetic acid, citric acid, succinic acid, glucuronic acid, and combinations thereof. "Acid" as used herein refers to the acid and any hydrate and salts thereof, i.e., citrates and succinates. Succinic acid is a preferred excipient for use in the present invention.

Examples of suitable saccharides include but are not limited to sucrose, trehalose, dextrose, mannitol, cyclodextrin and combinations thereof. Sucrose and cyclodextrin are preferred excipients for use in the present invention.

Examples of suitable amino acids include but are not limited to histidine, glycine, lysine, arginine and combinations thereof. Histidine and glycine are preferred excipients for use in the present invention.

Examples of suitable albumins include human serum albumin.

Examples of suitable polyethylene glycols are polyethylene glycols with a molecular weight of about 200 to 20,000 Da. Preferred polyethylene glycols are PEG 4000, PEG 5000, PEG 6000, PEG 8000, and PEG 10000.

Examples of suitable polysorbates are polysorbate 20 (TWEEN-20™) and polysorbate 80.

Examples of suitable cyclodextrins are alpha-, beta-, and gamma-cyclodextrin.

From the teachings of this invention, one of skill in the art can readily determine the excipients that would best provide a formulation that is substantially free of particles and/or aggregates, given a particular immunoconjugate solution.

Preferably, the tonicity of the immunoconjugate formulation is about that of human blood (i.e., isotonic).

Examples of suitable tonicifying agents are salts, amino acids, and sugars. Preferable salts include monovalent sodium salts. Preferable amino acids include histidine, glycine, lysine and arginine. Most preferred is glycine. Preferable sugars include monosaccharides, disaccharides, linear oligosaccharides, and cyclic oligosaccharides. A preferred disaccharide is sucrose. Suitable amounts of salts, saccharides, and/or amino acids can be added to the inventive formulation to achieve a desirable tonicity.

The pharmaceutical compound is an immunoconjugate composed of an antibody specifically recognizing a target cell antigen, and one or several covalently linked molecules of a cytotoxic drug, such as a maytansinoid, a taxane, or a CC-1065 analog.

The antibody can be specific for any kind of cell, but generally targets cells that are to be destroyed, such as tumor cells (particularly solid tumor cells), virus infected cells, microorganism infected cells, parasite infected cells, autoimmune cells (cells that produce autoantibodies), activated cells (those involved in graft rejection or graft vs. host disease), or any other type of diseased or abnormal cells.

Antibodies may be of any kind presently known, or that become known, and can include any immunoglobulin, any immunoglobulin fragment, such as Fab, F(ab')$_2$, dsFv, sFv, diabodies, and triabodies, or immunoglobulin chimera, which can bind to an antigen on the surface of a cell (e.g., which contains a complementarity determining region (CDR)). Any suitable antibody can be used as the cell-binding agent. One of ordinary skill in the art will appreciate that the selection of an appropriate antibody will depend upon the cell population to be targeted. In this regard, the type and number of cell surface molecules (i.e., antigens) that are selectively expressed in a particular cell population (typically and preferably a diseased cell population) will govern the selection of an appropriate antibody for use in the inventive composition. Cell surface expression profiles are known for a wide variety of cell types, including tumor cell types, or, if unknown, can be determined using routine molecular biology and histochemistry techniques.

The antibody can be polyclonal or monoclonal, but is most preferably a monoclonal antibody. As used herein, "polyclonal" antibodies refer to heterogeneous populations of antibody molecules, typically contained in the sera of immunized animals. "Monoclonal" antibodies refer to homogenous populations of antibody molecules that are specific to a particular antigen. Monoclonal antibodies are typically produced by a single clone of B lymphocytes ("B cells"). Monoclonal antibodies may be obtained using a variety of techniques known to those skilled in the art, including standard hybridoma technology (see, e.g., Köhler and Milstein, *Eur. J. Immunol.*, 5: 511-519 (1976), Harlow and Lane (eds.), *Antibodies: A Laboratory Manual*, CSH Press (1988), and C. A. Janeway et al. (eds.), *Immunobiology*, 5th Ed., Garland Publishing, New York, N.Y. (2001)). In brief, the hybridoma method of producing monoclonal antibodies typically involves injecting any suitable animal, typically and preferably a mouse, with an antigen (i.e., an "immunogen"). The animal is subsequently sacrificed, and B cells isolated from its spleen are fused with human myeloma cells. A hybrid cell is produced (i.e., a "hybridoma"), which proliferates indefinitely and continuously secretes high titers of an antibody with the desired specificity in vitro. Any appropriate method known in the art can be used to identify hybridoma cells that produce an antibody with the desired specificity. Such methods include, for example, enzyme-linked immunosorbent assay (ELISA), Western blot analysis, and radioimmunoassay. The population of hybridomas is screened to isolate individual clones, each of which secretes a single antibody species to the antigen. Because each hybridoma is a clone derived from fusion with a single B cell, all the antibody molecules it produces are identical in structure, including their antigen binding site and isotype. Monoclonal antibodies also may be generated using other suitable techniques including EBV-hybridoma technology (see, e.g., Haskard and Archer, *J. Immunol. Methods*, 74(2): 361-67 (1984), and Roder et al., *Methods Enzymol.*, 121: 140-67 (1986)), bacteriophage vector expression systems (see, e.g., Huse et al., *Science*, 246: 1275-81 (1989)), or phage display libraries comprising antibody fragments, such as Fab and scFv (single chain variable region) (see, e.g., U.S. Pat. Nos. 5,885,793 and 5,969,108, and International Patent Applications WO 92/01, 047 and WO 99/06,587).

The monoclonal antibody can be isolated from or produced in any suitable animal, but is preferably produced in a mammal, more preferably a mouse or human, and most preferably a human. Methods for producing an antibody in mice are well known to those skilled in the art and are described herein. With respect to human antibodies, one of ordinary skill in the art will appreciate that polyclonal antibodies can be isolated from the sera of human subjects vaccinated or immunized with an appropriate antigen. Alternatively, human antibodies can be generated by adapting known techniques for producing human antibodies in non-human animals such as mice (see, e.g., U.S. Pat. Nos. 5,545,806, 5,569,825, and 5,714,352, and U.S. Patent Application Publication No. 2002/0,197,266 A1).

While being the ideal choice for therapeutic applications in humans, human antibodies, particularly human monoclonal antibodies, typically are more difficult to generate than mouse monoclonal antibodies. Mouse monoclonal antibodies, however, induce a rapid host antibody response when administered to humans, which can reduce the therapeutic or diagnostic potential of the antibody-drug conjugate. To circumvent these complications, a monoclonal antibody preferably is not recognized as "foreign" by the human immune system.

To this end, phage display can be used to generate the antibody. In this regard, phage libraries encoding antigen-binding variable (V) domains of antibodies can be generated using standard molecular biology and recombinant DNA techniques (see, e.g., Sambrook et al. (eds.), *Molecular Cloning, A Laboratory Manual*, 3rd Edition, Cold Spring Harbor Laboratory Press, New York (2001)). Phage encoding a variable region with the desired specificity are selected for specific binding to the desired antigen, and a complete human antibody is reconstituted comprising the selected variable domain. Nucleic acid sequences encoding the reconstituted antibody are introduced into a suitable cell line, such as a myeloma cell used for hybridoma production, such that human antibodies having the characteristics of monoclonal antibodies are secreted by the cell (see, e.g., Janeway et al., supra, Huse et al., supra, and U.S. Pat. No. 6,265,150). Alternatively, monoclonal antibodies can be generated from mice that are transgenic for specific human heavy and light chain immunoglobulin genes. Such methods are known in the art and described in, for example, U.S. Pat. Nos. 5,545,806 and 5,569,825, and Janeway et al., supra.

Most preferably the antibody is a humanized antibody. As used herein, a "humanized" antibody is one in which the complementarity-determining regions (CDR) of a mouse monoclonal antibody, which form the antigen binding loops of the antibody, are grafted onto the framework of a human antibody molecule. Owing to the similarity of the frameworks of mouse and human antibodies, it is generally accepted in the art that this approach produces a monoclonal antibody that is antigenically identical to a human antibody but binds the same antigen as the mouse monoclonal antibody from which the CDR sequences were derived. Methods for generating humanized antibodies are well known in the art and are described in detail in, for example, Janeway et al., supra, U.S. Pat. Nos. 5,225,539, 5,585,089 and 5,693,761, European Patent No. 0,239,400 B1, and United Kingdom Patent No. 2,188,638. Humanized antibodies can also be generated using the antibody resurfacing technology described in U.S. Pat. No. 5,639,641 and Pedersen et al., *J. Mol. Biol.*, 235: 959-973 (1994). While the antibody employed in the immunoconjugate of the inventive composition most preferably is a humanized monoclonal antibody, a human monoclonal antibody and a mouse monoclonal antibody, as described above, are also within the scope of the invention.

Antibody fragments that have at least one antigen binding site, and thus recognize and bind to at least one antigen or receptor present on the surface of a target cell, also are within the scope of the invention. In this respect, proteolytic cleavage of an intact antibody molecule can produce a variety of antibody fragments that retain the ability to recognize and bind antigens. For example, limited digestion of an antibody molecule with the protease papain typically produces three fragments, two of which are identical and are referred to as the Fab fragments, as they retain the antigen binding activity of the parent antibody molecule. Cleavage of an antibody molecule with the enzyme pepsin normally produces two antibody fragments, one of which retains both antigen-binding arms of the antibody molecule, and is thus referred to as the F(ab')2 fragment. Reduction of a F(ab')$_2$ fragment with dithiothreitol or mercaptoethylamine produces a fragment referred to as a Fab' fragment. A single-chain variable region fragment (sFv) antibody fragment, which consists of a truncated Fab fragment comprising the variable (V) domain of an antibody heavy chain linked to a V domain of a light antibody chain via a synthetic peptide, can be generated using routine recombinant DNA technology techniques (see, e.g., Janeway et al., supra). Similarly, disulfide-stabilized variable region fragments (dsFv) can be prepared by recombinant DNA technology (see, e.g., Reiter et al., *Protein Engineering*, 7: 697-704 (1994)). Antibody fragments in the context of the invention, however, are not limited to these exemplary types of antibody fragments. Any suitable antibody fragment that recognizes and binds to a desired cell surface receptor or antigen can be employed. Antibody fragments are further described in, for example, Parham, *J. Immunol.*, 131: 2895-2902 (1983), Spring et al., *J. Immunol.*, 113: 470-478 (1974), and Nisonoff et al., *Arch. Biochem. Biophys.*, 89: 230-244 (1960). Antibody-antigen binding can be assayed using any suitable method known in the art, such as, for example, radioimmunoassay (RIA), ELISA, Western blot, immunoprecipitation, and competitive inhibition assays (see, e.g., Janeway et al., supra, and U.S. Patent Application Publication No. 2002/0,197,266 A1).

In addition, the antibody can be a chimeric antibody or an antigen binding fragment thereof. By "chimeric" it is meant that the antibody comprises at least two immunoglobulins, or fragments thereof, obtained or derived from at least two different species (e.g., two different immunoglobulins, such as a human immunoglobulin constant region combined with a murine immunoglobulin variable region). The antibody also can be a domain antibody (dAb) or an antigen binding fragment thereof, such as, for example, a camelid antibody (see, e.g., Desmyter et al., *Nature Struct. Biol.*, 3: 752, (1996)), or a shark antibody, such as, for example, a new antigen receptor (IgNAR) (see, e.g., Greenberg et al., *Nature*, 374:168 (1995), and Stanfield et al., *Science*, 305: 1770-1773 (2004)).

Any suitable antibody can be used in the context of the invention. For example, the monoclonal antibody J5 is a murine IgG2a antibody that is specific for Common Acute Lymphoblastic Leukemia Antigen (CALLA) (Ritz et al., *Nature*, 283: 583-585 (1980)), and can be used to target cells that express CALLA (e.g., acute lymphoblastic leukemia cells). The monoclonal antibody MY9 is a murine IgG1 antibody that binds specifically to the CD33 antigen (Griffin et al., *Leukemia Res.*, 8: 521 (1984)), and can be used to target cells that express CD33 (e.g., acute myelogenous leukemia (AML) cells).

Similarly, the monoclonal antibody anti-B4 (also referred to as B4) is a murine IgG1 antibody that binds to the CD19 antigen on B cells (Nadler et al., *J. Immunol.*, 131: 244-250 (1983)), and can be used to target B cells or diseased cells that express CD19 (e.g., non-Hodgkin's lymphoma cells and chronic lymphoblastic leukemia cells). N901 is a murine monoclonal antibody that binds to the CD56 (neural cell adhesion molecule) antigen found on cells of neuroendocrine origin, including small cell lung tumor, which can be used in the immunoconjugate to target drugs to cells of neuroendocrine origin. The J5, MY9, and B4 antibodies preferably are resurfaced or humanized prior to their use as part of the immunoconjugate. Resurfacing or humanization of antibodies is described in, for example, Roguska et al., *Proc. Natl. Acad. Sci. USA*, 91: 969-73 (1994).

In addition, the monoclonal antibody C242 binds to the CanAg antigen (see, e.g., U.S. Pat. No. 5,552,293), and can be used to target the immunoconjugate to CanAg expressing tumors, such as colorectal, pancreatic, non-small cell lung, and gastric cancers. HuC242 is a humanized form of the monoclonal antibody C242 (see, e.g., U.S. Pat. No. 5,552, 293). The hybridoma from which HuC242 is produced is deposited with ECACC identification Number 90012601. HuC242 can be prepared using CDR-grafting methodology (see, e.g., U.S. Pat. Nos. 5,585,089, 5,693,761, and 5,693, 762) or resurfacing technology (see, e.g., U.S. Pat. No. 5,639, 641). HuC242 can be used to target the immunoconjugate to tumor cells expressing the CanAg antigen, such as, for example, colorectal, pancreatic, non-small cell lung, and gastric cancer cells.

To target ovarian cancer and prostate cancer cells, an anti-MUC1 antibody can be used as the cell-binding agent in the immunoconjugate. Anti-MUC1 antibodies include, for example, anti-HMFG-2 (see, e.g., Taylor-Papadimitriou et al., *Int. J. Cancer*, 28: 17-21 (1981)), hCTM01 (see, e.g., van Hofet al., *Cancer Res.*, 56: 5179-5185 (1996)), and DS6. Prostate cancer cells also can be targeted with the immunoconjugate by using an anti-prostate-specific membrane antigen (PSMA) as the cell-binding agent, such as J591 (see, e.g., Liu et al., *Cancer Res.*, 57: 3629-3634 (1997)). Moreover, cancer cells that express the Her2 antigen, such as breast, prostate, and ovarian cancers, can be targeted using the antibody trastuzumab. Anti-IGF-IR antibodies that bind to insulin-like growth factor receptor also can be used in the immunoconjugate.

Particularly preferred antibodies are humanized monoclonal antibodies, examples of which include huN901, huMy9-6, huB4, huC242, DS6, trastuzumab, bivatuzumab, sibrotuzumab, and rituximab (see, e.g., U.S. Pat. Nos. 5,639,641 and 5,665,357; U.S. Patent Application Publication No. 2005-0118183 A1, International Patent Application WO 02/16,401, Pedersen et al., supra, Roguska et al., supra, Liu et al., supra, Nadler et al., supra, Colomer et al., *Cancer Invest.*, 19: 49-56 (2001), Heider et al., *Eur. J. Cancer*, 31A: 2385-2391 (1995), Welt et al., *J. Clin. Oncol.*, 12: 1193-1203 (1994), and Maloney et al., *Blood*, 90: 2188-2195 (1997)). Most preferably, the antibody is the huN901 humanized monoclonal antibody or the huMy9-6 humanized monoclonal antibody. Other humanized monoclonal antibodies are known in the art and can be used in connection with the invention.

The immunoconjugate can comprise any suitable drug, typically a cytotoxic agent. A "cytotoxic agent," as used herein, refers to any compound that results in the death of a cell, induces cell death, or decreases cell viability. Suitable cytotoxic agents include, for example, maytansinoids and maytansinoid analogs, taxoids, CC-1065 and CC-1065 analogs, and dolastatin and dolastatin analogs. In a preferred embodiment of the invention, the cytotoxic agent is a maytansinoid, including maytansinol and maytansinol analogs. Maytansinoids are compounds that inhibit microtubule formation and are highly toxic to mammalian cells. Examples of suitable maytansinol analogues include those having a modified aromatic ring and those having modifications at other positions. Such maytansinoids are described in, for example, U.S. Pat. Nos. 4,256,746, 4,294,757, 4,307,016, 4,313,946, 4,315,929, 4,322,348, 4,331,598, 4,361,650, 4,362,663, 4,364,866, 4,424,219, 4,371,533, 4,450,254, 5,475,092, 5,585,499, 5,846,545, and 6,333,410.

Examples of maytansinol analogs having a modified aromatic ring include: (1) C 19-dechloro (U.S. Pat. No. 4,256,746) (prepared by LAH reduction of ansamytocin P2), (2) C-20-hydroxy (or C-20-demethyl)+/−C-19-dechloro (U.S. Pat. Nos. 4,361,650 and 4,307,016) (prepared by demethylation using Streptomyces or Actinomyces or dechlorination using LAH), and (3) C-20-demethoxy, C-20-acyloxy (—OCOR), +/−dechloro (U.S. Pat. No. 4,294,757) (prepared by acylation using acyl chlorides).

Examples of maytansinol analogs having modifications of positions other than an aromatic ring include: (1) C-9-SH (U.S. Pat. No. 4,424,219) (prepared by the reaction of maytansinol with $H_2S$ or $P_2S_5$), (2) C-14-alkoxymethyl (demethoxy/$CH_2OR$) (U.S. Pat. No. 4,331,598), (3) C-14-hydroxymethyl or acyloxymethyl ($CH_2OH$ or $CH_2OAc$) (U.S. Pat. No. 4,450,254) (prepared from Nocardia), (4) C-15-hydroxy/acyloxy (U.S. Pat. No. 4,364,866) (prepared by the conversion of maytansinol by Streptomyces), (5) C-15-methoxy (U.S. Pat. Nos. 4,313,946 and 4,315,929) (isolated from Trewia nudiflora), (6) C-18-N-demethyl (U.S. Pat. Nos. 4,362,663 and 4,322,348) (prepared by the demethylation of maytansinol by Streptomyces), and (7) 4,5-deoxy (U.S. Pat. No. 4,371,533) (prepared by the titanium trichloride/LAH reduction of maytansinol).

In a preferred embodiment of the invention, the immunoconjugate utilizes the thiol-containing maytansinoid DM1, also known as N2'-deacetyl-N2'-(3-mercapto-1-oxopropyl)-maytansine, as the cytotoxic agent. The structure of DM1 is represented by formula (I):

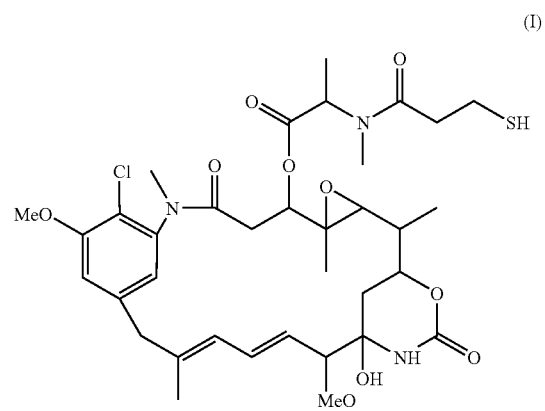 [SMILES: COc1cc2cc(c1Cl)N(C)C(=O)CC(OC(=O)C(C)N(C)C(=O)CCS)C1(C)OC1C(C)C1CC(O)(NC(=O)O1)C(OC)/C=C/C=C(\C)C2]

In another preferred embodiment of the invention, the immunoconjugate utilizes the thiol-containing maytansinoid DM4, also known as N-2'-deacetyl-N-2'-(4-methyl-4-mercapto-1-oxopentyl)-maytansine, as the cytotoxic agent. The structure of DM4 is represented by formula (II):

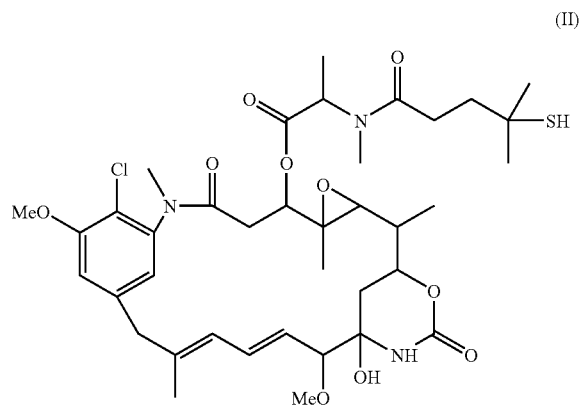 [SMILES: COc1cc2cc(c1Cl)N(C)C(=O)CC(OC(=O)C(C)N(C)C(=O)CCC(C)(C)S)C1(C)OC1C(C)C1CC(O)(NC(=O)O1)C(OC)/C=C/C=C(\C)C2]

Other maytansines may be used in the context of the invention, including, for example, thiol and disulfide-containing maytansinoids bearing a mono or di-alkyl substitution on the carbon atom bearing the sulfur atom. Particularly preferred is a maytansinoid having at the $C_3$ position, the $C_{14}$ hydroxymethyl, the $C_{15}$ hydroxy, or the $C_{20}$ desmethyl functionality, an acylated amino acid side chain with an acyl group bearing a hindered sulfhydryl group, wherein the carbon atom of the acyl group bearing the thiol functionality has one or two substituents, said substituents being $CH_3$, $C_2H_5$, linear or branched alkyl or alkenyl having from 1 to 10 carbon atoms, cyclic alkyl or alkenyl having from 3 to 10 carbon atoms, phenyl, substituted phenyl, or heterocyclic aromatic or heterocyclic radical, and further wherein one of the substituents can be H, and wherein the acyl group has a linear chain length of at least three carbon atoms between the carbonyl functionality and the sulfur atom.

Additional maytansines for use in the context of the invention include compounds represented by formula (III):

(III)

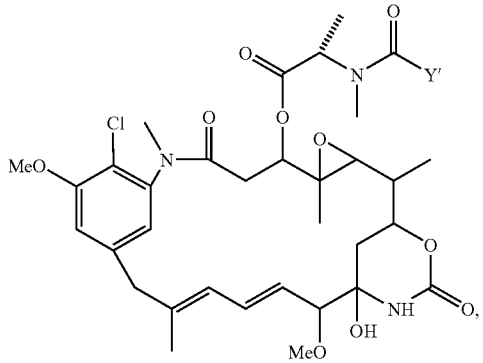

wherein Y' represents
$(CR_7R_8)_l(CR_9{=}CR_{10})_p(C{\equiv}C)_qA_o(CR_5R_6)_mD_u(CR_{11}{=}CR_{12})_r(C{\equiv}C)_sB_t(CR_3R_4)_n—CR_1R_2SZ$, wherein $R_1$ and $R_2$ are each independently linear alkyl or alkenyl having from 1 to 10 carbon atoms, preferably $CH_3$ or $C_2H_5$, branched or cyclic alkyl or alkenyl having from 3 to 10 carbon atoms, phenyl, substituted phenyl or heterocyclic aromatic or heterocyclic radical, and wherein $R_2$ also can be H, wherein A, B, D are cycloalkyl or cycloalkenyl having 3-10 carbon atoms, simple or substituted aryl, or heterocyclic aromatic, or heterocyclic radical, wherein $R_3$, $R_4$, $R_5$, $R_6$, $R_7$, $R_8$, $R_9$, $R_{10}$, $R_{11}$, and $R_{12}$ are each independently H, linear alkyl or alkenyl having from 1 to 10 carbon atoms, preferably $CH_3$ or $C_2H_5$, branched or cyclic alkyl or alkenyl having from 3 to 10 carbon atoms, phenyl, substituted phenyl or heterocyclic aromatic, or heterocyclic radical, wherein l, m, n, o, p, q, r, s, and u, are each independently zero or an integer from 1 to 5, provided that at least two of l, m, n, o, p, q, r, s, t and u, are not zero at any one time, and wherein Z is H, SR or COR, wherein R is linear alkyl or alkenyl having from 1 to 10 carbon atoms, branched or cyclic alkyl or alkenyl having from 3 to 10 carbon atoms, simple or substituted aryl or heterocyclic aromatic, or heterocyclic radical.

Preferred embodiments of formula (III) include compounds of formula (III) wherein (a) $R_1$ is methyl, $R_2$ is H and Z is H, (b) $R_1$ and $R_2$ are methyl and Z is H, (c) $R_1$ is methyl, $R_2$ is H, and Z is —$SCH_3$, and (d) $R_1$ and $R_2$ are methyl, and Z is —$SCH_3$.

Such additional maytansines also include compounds represented by formula (IV-L), (IV-D), or (IV-D,L):

(IV-L)

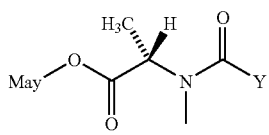

(IV-D)

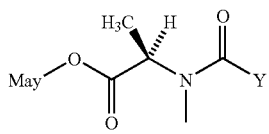

(IV-D,L)

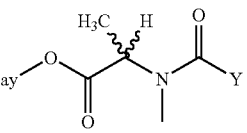

wherein Y represents $(CR_7R_8)_l(CR_5R_6)_m(CR_3R_4)_n CR_1R_2SZ$, wherein $R_1$ and $R_2$ are each independently H, linear alkyl, or alkenyl having from 1 to 10 carbon atoms, preferably $CH_3$ or $C_2H_5$, branched or cyclic alkyl or alkenyl having from 3 to 10 carbon atoms, phenyl, substituted phenyl, or heterocyclic aromatic or heterocyclic radical, wherein $R_3$, $R_4$, $R_5$, $R_6$, $R_7$, and $R_8$ are each independently H, linear alkyl or alkenyl having from 1 to 10 carbon atoms, preferably $CH_3$ or $C_2H_5$, branched or cyclic alkyl or alkenyl having from 3 to 10 carbon atoms, phenyl, substituted phenyl, or heterocyclic aromatic or heterocyclic radical, wherein l, m, and n are each independently an integer of from 1 to 5, and in addition n can be zero, wherein Z is H, SR, or COR wherein R is methyl, linear or branched alkyl or alkenyl having from 1 to 10 carbon atoms, cyclic alkyl or alkenyl having from 3 to 10 carbon atoms, or simple or substituted aryl or heterocyclic aromatic or heterocyclic radical, and wherein May represents a maytansinoid which bears the side chain at C-3, C-14 hydroxymethyl, C-15 hydroxy, or C-20 desmethyl.

Preferred embodiments of formulas (IV-L), (IV-D) and (IV-D,L) include compounds of formulas (IV-L), (IV-D) and (IV-D,L) wherein (a) $R_1$ is H, $R_2$ is methyl, $R_5$, $R_6$, $R_7$, and $R_8$ are each H, l and m are each 1, n is 0, and Z is H, (b) $R_1$ and $R_2$ are methyl, $R_5$, $R_6$, $R_7$, $R_8$ are each H, l and m are l, n is 0, and Z is H, (c) $R_1$ is H, $R_2$ is methyl, $R_5$, $R_6$, $R_7$, and $R_8$ are each H, l and m are each l, n is 0, and Z is —$SCH_3$, or (d) $R_1$ and $R_2$ are methyl, $R_5$, $R_6$, $R_7$, $R_8$ are each H, l and m are 1, n is 0, and Z is —$SCH_3$.

Preferably the cytotoxic agent is represented by formula (IV-L).

Additional preferred maytansines also include compounds represented by formula (V):

(V)

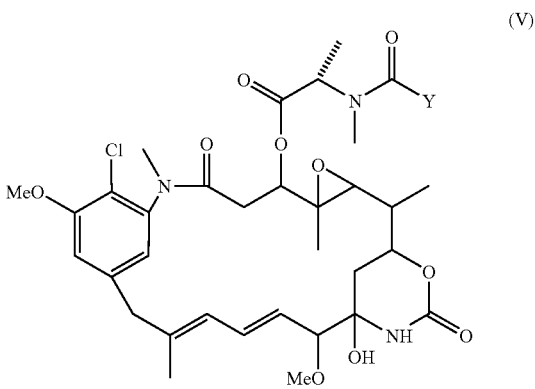

wherein Y represents $(CR_7R_8)_l(CR_5R_6)_m(CR_3R_4)_n CR_1R_2SZ$, wherein $R_1$ and $R_2$ are each independently H, linear alkyl, or alkenyl having from 1 to 10 carbon atoms, preferably $CH_3$ or $C_2H_5$, branched or cyclic alkyl or alkenyl having from 3 to 10 carbon atoms, phenyl, substituted phenyl or heterocyclic aromatic or heterocyclic radical, wherein $R_3$, $R_4$, $R_5$, $R_6$, $R_7$, and $R_8$ are each independently H, linear alkyl or alkenyl having from 1 to 10 carbon atoms, preferably $CH_3$ or $C_2H_5$, branched or cyclic alkyl or alkenyl having from 3 to 10 carbon atoms, phenyl, substituted phenyl, or heterocyclic aromatic or heterocyclic radical, wherein l, m, and n are each independently an integer of from 1 to 5, and in addition n can be zero, and wherein Z is H, SR or —COR, wherein R is methyl, linear alkyl or alkenyl having from 1 to 10 carbon atoms, branched or cyclic alkyl or alkenyl having from 3 to 10 carbon atoms, or simple or substituted aryl or heterocyclic aromatic or heterocycloalic radical.

Preferred embodiments of formula (V) include compounds of formula (V) wherein (a) $R_1$ is H, $R_2$ is methyl, $R_5$, $R_6$, $R_7$, and $R_8$ are each H; l and m are each 1; n is 0; and Z is H, (b) $R_1$ and $R_2$ are methyl; $R_5$, $R_6$, $R_7$, $R_8$ are each H, l and m are 1; n is 0; and Z is H, (c) $R_1$ is H, $R_2$ is methyl, $R_5$, $R_6$, $R_7$, and $R_8$ are each H, l and m are each 1, n is 0, and Z is —$SCH_3$, or (d) $R_1$ and $R_2$ are methyl, $R_5$, $R_6$, $R_7$, R are each H, l and m are 1,n is 0, and Z is-$SCH_3$.

Still further preferred maytansines include compounds represented by formula (VI-L), (VI-D), or (VI-D,L):

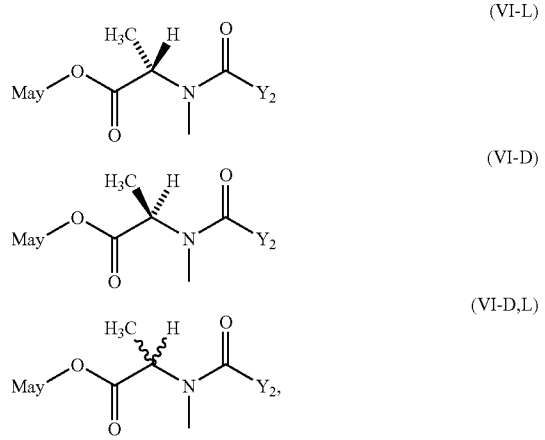

wherein $Y_2$ represents $(CR_7R_8)_l(CR_5R_6)_m(CR_3R_4)_n CR_1R_2SZ_2$, wherein $R_1$ and $R_2$ are each independently linear alkyl or alkenyl having from 1 to 10 carbon atoms, preferably $CH_3$ or $C_2H_5$, branched or cyclic alkyl or alkenyl having from 3 to 10 carbon atoms, phenyl, substituted phenyl or heterocyclic aromatic or heterocyclic radical, and wherein $R_2$ also can be H, wherein $R_3$, $R_4$, $R_5$, $R_6$, $R_7$, and $R_8$ are each independently H, linear cyclic alkyl or alkenyl having from 1 to 10 carbon atoms, preferably $CH_3$ or $C_2H_5$, branched or cyclic alkyl or alkenyl having from 3 to 10 carbon atoms, phenyl, substituted phenyl or heterocyclic aromatic or heterocyclic radical, wherein l, m, and n are each independently an integer of from 1 to 5, and in addition n can be zero, wherein $Z_2$ is SR or COR, wherein R is linear alkyl or alkenyl having from 1 to 10 carbon atoms, branched or cyclic alkyl or alkenyl having from 3 to 10 carbon atoms, or simple or substituted aryl or heterocyclic aromatic or heterocyclic radical, and wherein May is a maytansinoid.

Additional preferred maytansines include compounds represented by formula (VII):

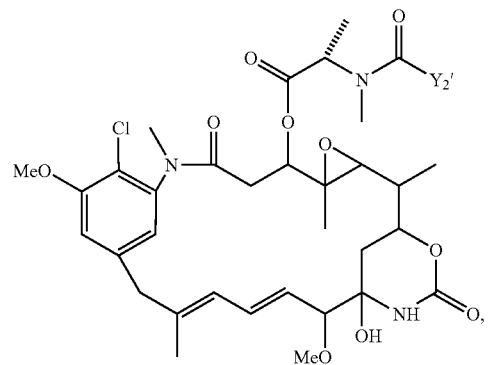

wherein $Y_2$, represents
$(CR_7R_8)_l(CR_9\!=\!CR_{10})_p(C\!\equiv\!C)_qA_o(CR_5R_6)_mD_u (CR_{11}\!=\!CR_{12})_r(C\!\equiv\!C)_sB_t(CR_3R_4)_nCR_1R_2SZ_2$, wherein $R_1$ and $R_2$ are each independently H, linear branched or alkyl or alkenyl having from 1 to 10 carbon atoms, preferably $CH_3$ or $C_2H_5$, cyclic alkyl or alkenyl having from 3 to 10 carbon atoms, phenyl, substituted phenyl or heterocyclic aromatic or heterocyclic radical, wherein A, B, and D each independently is cycloalkyl or cycloalkenyl having 3 to 10 carbon atoms, simple or substituted aryl, or heterocyclic aromatic or heterocyclic radical, wherein $R_3$, $R_4$, $R_5$, $R_6$, $R_7$, $R_8$, $R_9$, $R_{10}$, $R_{11}$, and $R_{12}$ are each independently H, linear alkyl or alkenyl having from 1 to 10 carbon atoms, preferably $CH_3$ or $C_2H_5$, branched or cyclic alkyl or alkenyl having from 3 to 10 carbon atoms, phenyl, substituted phenyl or heterocyclic aromatic or heterocyclic radical, wherein l, m, n, o, p, q, r, s, t, and u are each independently zero or an integer of from 1 to 5, provided that at least two of l, m, n, o, p, q, r, s, t, and u are not zero at any one time, and wherein $Z_2$ is SR or —COR, wherein R is linear alkyl or alkenyl having from 1 to 10 carbon atoms, branched or cyclic alkyl or alkenyl having from 3 to 10 carbon atoms, or simple or substituted aryl or heterocyclic aromatic or heterocyclic radical.

Preferred embodiments of formula (VII) include compounds of formula (VII), wherein $R_1$ is methyl and $R_2$ is H.

In addition to maytansinoids, the cytotoxic agent used in the immunoconjugate can be a taxane or derivative thereof. Taxanes are a family of compounds that includes paclitaxel (Taxol®), a cytotoxic natural product, and docetaxel (Taxotere®), a semi-synthetic derivative, which are both widely used in the treatment of cancer. Taxanes are mitotic spindle poisons that inhibit the depolymerization of tubulin, resulting in cell death. While docetaxel and paclitaxel are useful agents in the treatment of cancer, their antitumor activity is limited because of their non-specific toxicity towards normal cells. Further, compounds like paclitaxel and docetaxel themselves are not sufficiently potent to be used in immunoconjugates.

A preferred taxane for use in the preparation of a cytotoxic immunoconjugate is the taxane of formula (VIII):

(VIII)

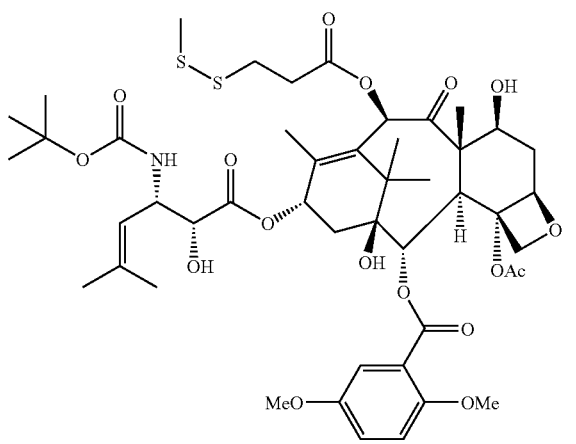

Methods for synthesizing taxanes that can be used in the context of the invention, along with methods for conjugating taxanes to cell-binding agents such as antibodies, are described in detail in U.S. Pat. Nos. 5,416,064, 5,475,092, 6,340,701, 6,372,738, 6,436,931, 6,596,757, 6,706,708, and 6,716,821, and in U.S. Patent Application Publication No. 2004/0,024,049 A1.

The cytotoxic agent also can be CC-1065 or a derivative thereof. CC-1065 is a potent anti-tumor antibiotic isolated from the culture broth of Streptomyces zelensis. CC-1065 is about 1000-fold more potent in vitro than commonly used anti-cancer drugs, such as doxorubicin, methotrexate, and vincristine (Bhuyan et al., *Cancer Res.*, 42: 3532-3537 (1982)). CC-1065 and its analogs are disclosed in U.S. Pat. Nos. 5,585,499, 5,846,545, 6,340,701, and 6,372,738. The cytotoxic potency of CC-1065 has been correlated with its alkylating activity and its DNA-binding or DNA-intercalating activity. These two activities reside in separate parts of the molecule. In this respect, the alkylating activity is contained in the cyclopropapyrroloindole (CPI) subunit and the DNA-binding activity resides in the two pyrroloindole subunits of CC-1065.

Several CC-1065 analogs are known in the art and also can be used as the cytotoxic agent in the immunoconjugate (see, e.g., Warpehoski et al., *J. Med. Chem.*, 31: 590-603 (1988)). A series of CC-1065 analogs has been developed in which the CPI moiety is replaced by a cyclopropabenzindole (CBI) moiety (Boger et al., *J. Org. Chem.*, 55: 5823-5833 (1990), and Boger et al., *Bioorg. Med. Chem. Lett.*, 1: 115-120 (1991)). These CC-1065 analogs maintain the high in vitro potency of the parental drug, without causing delayed toxicity in mice. Like CC-1065, these compounds are alkylating agents that covalently bind to the minor groove of DNA to cause cell death.

The therapeutic efficacy of CC-1065 analogs can be greatly improved by changing the in vivo distribution through targeted delivery to a tumor site, resulting in lower toxicity to non-targeted tissues, and thus, lower systemic toxicity. To this end, conjugates of analogs and derivatives of CC-1065 with cell-binding agents that specifically target tumor cells have been generated (see, e.g., U.S. Pat. Nos. 5,475,092, 5,585, 499, and 5,846,545). These conjugates typically display high target-specific cytotoxicity in vitro, and anti-tumor activity in human tumor xenograft models in mice (see, e.g., Chari et al., *Cancer Res.*, 55: 4079-4084 (1995)).

Methods for synthesizing CC-1065 analogs are described in detail in U.S. Pat. Nos. 5,475,092, 5,585,499, 5,846,545, 6,534,660, 6,586,618, and 6,756,397 and U.S. Patent Application Publication No. 2003/0,195,365 A1.

Drugs such as methotrexate, daunorubicin, doxorubicin, vincristine, vinblastine, melphalan, mitomycin C, chlorambucil, calicheamicin, tubulysin and tubulysin analogs, duocarmycin and duocarmycin analogs, dolastatin and dolastatin analogs also can be used in the context of the invention. Doxarubicin and daunorubicin compounds (see, e.g., U.S. Pat. No. 6,630,579) can also be used as the drug.

The immunoconjugates may be prepared by in vitro methods. In order to link a drug or prodrug to the antibody, a linking group is used. Suitable linking groups are well known in the art and include disulfide groups, acid labile groups, photolabile groups, peptidase labile groups, and esterase labile groups. Preferred linking groups are disulfide groups. For example, immunoconjugates can be constructed using a disulfide exchange reaction between the antibody and the drug or prodrug. The drug molecules also can be linked to an antibody through an intermediary carrier molecule such as serum albumin.

The antibody may be modified by reaction with a bifunctional crosslinking reagent, thereby resulting in the covalent attachment of a linker molecule to the antibody. As used herein, a "bifunctional crosslinking reagent" is any chemical moiety that covalently links a cell-binding agent to a drug, such as the drugs described herein. In a preferred embodiment of the invention, a portion of the linking moiety is provided by the drug. In this respect, the drug comprises a linking moiety that is part of a larger linker molecule that is used to join the antibody to the drug. For example, to form the maytansinoid DM1, the side chain at the C-3 hydroxyl group of maytansine is modified to have a free sulfhydryl group (SH). This thiolated form of maytansine can react with a modified antibody to form an immunoconjugate. Therefore, the final linker is assembled from two components, one of which is provided by the crosslinking reagent, while the other is provided by the side chain from DM1.

Any suitable bifunctional crosslinking reagent can be used in connection with the invention, so long as the linker reagent provides for retention of the therapeutic, e.g., cytotoxicity, and targeting characteristics of the drug and the antibody, respectively. Preferably, the linker molecule joins the drug to the antibody through chemical bonds (as described above), such that the drug and the antibody are chemically coupled (e.g., covalently bonded) to each other. Preferably, the linking reagent is a cleavable linker. More preferably, the linker is cleaved under mild conditions, i.e., conditions within a cell under which the activity of the drug is not affected. Examples of suitable cleavable linkers include disulfide linkers, acid labile linkers, photolabile linkers, peptidase labile linkers, and esterase labile linkers. Disulfide containing linkers are linkers cleavable through disulfide exchange, which can occur under physiological conditions. Acid labile linkers are linkers cleavable at acid pH. For example, certain intracellular compartments, such as endosomes and lysosomes, have an acidic pH (pH 4-5), and provide conditions suitable to cleave acid labile linkers. Photo labile linkers are useful at the body surface and in many body cavities that are accessible to light. Furthermore, infrared light can penetrate tissue. Peptidase labile linkers can be used to cleave certain peptides inside or outside cells (see e.g., Trouet et al., *Proc. Natl. Acad. Sci. USA*, 79: 626-629 (1982), and Umemoto et al., *Int. J. Cancer*, 43: 677-684 (1989)).

Preferably the drug is linked to an antibody through a disulfide bond. The linker molecule comprises a reactive chemical group that can react with the antibody. Preferred reactive chemical groups for reaction with the antibody are N-succinimidyl esters and N-sulfosuccinimidyl esters. Additionally the linker molecule comprises a reactive chemical group, preferably a dithiopyridyl group, that can react with the drug to form a disulfide bond. Particularly preferred linker molecules include, for example, N-succinimidyl 3-(2-pyridyldithio)propionate (SPDP) (see, e.g., Carlsson et al., *Biochem. J,* 173: 723-737 (1978)), N-succinimidyl 4-(2-pyridyldithio)butanoate (SPDB) (see, e.g., U.S. Pat. No. 4,563, 304), and N-succinimidyl 4-(2-pyridyldithio)pentanoate (SPP) (see, e.g., CAS Registry number 341498-08-6).

While cleavable linkers preferably are used in the inventive method, a non-cleavable linker also can be used to generate the above-described immunoconjugate. A non-cleavable linker is any chemical moiety that is capable of linking a drug, such as a maytansinoid, a taxane, or a CC-1065 analog, to a cell-binding agent, such as an antibody, in a stable, covalent manner. Thus, non-cleavable linkers are substantially resistant to acid-induced cleavage, light-induced cleavage, peptidase-induced cleavage, esterase-induced cleavage, and disulfide bond cleavage, at conditions under which the drug or the antibody remains active.

Suitable crosslinking reagents that form non-cleavable linkers between a drug and a cell-binding agent are well known in the art. Examples of non-cleavable linkers include linkers having an N-succinimidyl ester or N-sulfosuccinimidyl ester moiety for reaction with the cell-binding agent, as well as a maleimido- or haloacetyl-based moiety for reaction with the drug. Crosslinking reagents comprising a maleimido-based moiety include N-succinimidyl 4-(maleimidomethyl)cyclohexanecarboxylate (SMCC), N-succinimidyl-4-(N-maleimidomethyl)-cyclohexane-1-carboxy-(6-amidocaproate), which is a "long chain" analog of SMCC (LC-SMCC), κ-maleimidoundecanoic acid N-succinimidyl ester (KMUA), γ-maleimidobutyric acid N-succinimidyl ester (GMBS), ε-maleimidocaproic acid N-hydroxysuccinimide ester (EMCS), m-maleimidobenzoyl-N-hydroxysuccinimide ester (MBS), N-α-maleimidoacetoxy)-succinimide ester (AMAS), succinimidyl-6-(β-maleimidopropionamido) hexanoate (SMPH), N-succinimidyl 4-(p-maleimidophenyl)-butyrate (SMPB), and N-(p-maleimidophenyl)isocyanate (PMPI). Cross-linking reagents comprising a haloacetyl-based moiety include N-succinimidyl-4-(iodoacetyl)-aminobenzoate (SIAB), N-succinimidyl iodoacetate (SIA), N-succinimidyl bromoacetate (SBA), and N-succinimidyl 3-(bromoacetamido)propionate (SBAP).

Other crosslinking reagents lacking a sulfur atom that form non-cleavable linkers can also be used in the inventive method. Such linkers can be derived from dicarboxylic acid based moieties. Suitable dicarboxylic acid based moieties include, but are not limited to, α,ω-dicarboxylic acids of the general formula (IX):

HOOC—$X_l$-$Y_n$-$Z_m$-COOH  (IX), wherein X is a linear or branched alkyl, alkenyl, or alkynyl group having 2 to 20 carbon atoms, Y is a cycloalkyl or cycloalkenyl group bearing 3 to 10 carbon atoms, Z is a substituted or unsubstituted aromatic group bearing 6 to 10 carbon atoms, or a substituted or unsubstituted heterocyclic group wherein the hetero atom is selected from N, O or S, and wherein l, m, and n are each 0 or 1, provided that l, m, and n are all not zero at the same time.

Many of the non-cleavable linkers disclosed herein are described in detail in U.S. Patent Application Publication No. 2005-0169933 A1.

Alternatively, as disclosed in U.S. Pat. No. 6,441,163 B1, the drug can be first modified to introduce a reactive ester suitable to react with an antibody. Reaction of these maytansinoids containing an activated linker moiety with an antibody provides another method of producing a cleavable or non-cleavable antibody maytansinoid conjugate.

Processes for the manufacture of such pharmaceutical compositions involve buffer exchanging the bulk pharmaceutical into appropriate formulation buffer by chromatography or diafiltration and then adding appropriate excipients in desired amount, either as solution or as solid. Final adjustment of protein concentration and/or pH may also be performed to achieve the desired composition.

The immunoconjugates of the invention are administered to the patient in the form of a pharmaceutical formulation described in this application and a pharmaceutically acceptable carrier, excipient or diluent therefore. As used, "pharmaceutically acceptable" refers to those agents that are useful in the treatment or diagnosis of mammals, preferably human. The preferred mode of administration is parenterally, particularly by the intravenous, intramuscular, subcutaneous, intraperitoneal, or intralymphatic route. See, e.g. *Remington's Pharmaceutical Sciences,* 16th ed., 1980, Mack Publishing Company, edited by Osol et al. Such compositions may include proteins, such as serum proteins, for example, human serum albumin, buffers or buffering substances such as phosphates, other salts, or electrolytes, and the like. Suitable diluents may include, for example, sterile water, isotonic saline, dilute aqueous dextrose, a polyhydric alcohol or mixtures of such alcohols, for example, glycerin, propylene glycol, polyethylene glycol and the like. The formulations may contain preservatives such as phenethyl alcohol, methyl and propyl parabens, and the like. If desired, the formulation can include 0.05 to about 0.20 percent by weight of an antioxidant.

Administration may be via any route known to be effective by the physician of ordinary skill. Parenteral administration is preferred. Preferred parenteral routes for administering the formulations of the present invention include intravenous, intramuscular, subcutaneous, intraperitoneal, intraarterial. Intravenous, intraperitoneal, intramuscular, and subcutaneous routes of administration of the compounds used in the present invention are more preferred parenteral routes of administration. Intravenous, intraperitoneal, and subcutaneous routes of administration of the formulations of the present invention yet more highly preferred.

Administration via certain parenteral routes may involve introducing the formulations of the present invention into the body of a patient through a needle or a catheter. Optionally, such administration may be propelled by a sterile syringe or some other mechanical device such as a continuous infusion system. A formulation provided by the present invention may be administered using a syringe, injector, pump, or any other device or by gravity recognized in the art for parenteral administration. The formulation can be administered parenterally, in sterile liquid dosage forms. These formulation may be administered intravenously as a bolus or rapid infusion, which can, in addition to their desired therapeutic, diagnostic or medicinal effect, cause the release of immunoconjugate.

The immunoconjugates of the invention are effective over a wide dosage range depending on factors such as the disease state to be treated or the biological effect to be modified, the manner in which the immunoconjugate is administered, the age, weight and condition of the patient as well as other factors to be determined by the treating physician. Thus, the amount administered to any given patient can be determined on an individual basis.

The amount of a formulation of the present invention that is administered to treat a patient may depend on a number of factors, among which are included, without limitation, the patient's sex, weight and age, the underlying causes of the condition or disease to be treated, the route of administration and bioavailability, the persistence of the administered immunoconjugate in the body, the formulation, and the potency of the immunoconjugate. Where administration is intermittent, the amount per administration should also take into account the interval between doses, and the bioavailability of the immunoconjugate from the formulation. Administration of the formulation of the present invention could be continuous. It is within the skill of the ordinary physician to titrate the dose and infusion rate or frequency of administration of the formulation of the present invention to achieve the desired clinical result.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of therapeutically-significant-compound can be about 0.1 to 100 milligrams per kilogram of body weight.

Dosage forms suitable for internal administration contain from about 1 milligram to about 500 milligrams of therapeutically-significant-compound per unit. In these pharmaceutical compositions the therapeutically-significant-compound ordinarily will be present in an amount of about 0.05-2% by weight in a liquid formulation and 2-50% in the lyophilized formulation prior to reconstitution based on the total weight of the composition.

The present invention also provides for a lyophilized powder of the above-described formulation. Preferably, the lyophilized formulation comprises one or more additional components, such as a lyoprotectant and/or a bulking agent. The lyophilized powder can be reconstituted with water to create a reconstituted solution. The present formulation can be lyophilized and reconstituted as described in U.S. Patent Application No. 2004/0,241,174 A1, which description is hereby incorporated by reference, and which describes lyophilized formulations comprising immunoconjugates.

Prior to reconstitution of the lyophilized composition, the relative amounts of each component comprising the inventive lyophilized composition can be described in terms of mg of excipient (e.g., buffer, surfactant, bulking agent, cryoprotectant) per mg of conjugate.

While any suitable buffering agent described herein can be used in connection with the inventive lyophilized composition, the lyophilized composition preferably comprises a sodium succinate buffer. The buffering agent can be present in the inventive lyophilized composition in any suitable amount. In particular, the lyophilized composition desirably comprises about 0.1 mg to about 2 mg of the buffering agent per mg of the conjugate (e.g., about 0.1 mg to about 0.5 mg buffering agent per mg of the conjugate, about 0.5 mg to about 1 mg buffering agent per mg of the conjugate, or about 1 mg to about 2 mg buffering agent per mg of the conjugate). Most preferably, the lyophilized composition comprises about 0.3 mg sodium succinate buffer per mg of the conjugate.

The lyophilized composition desirably comprises about 0.005 mg to about 0.1 mg of polysorbate per mg of the conjugate, and preferably about 0.005 mg to about 0.01 mg polysorbate per mg of the conjugate, 0.01 mg to about 0.05 mg polysorbate per mg of the conjugate, or about 0.05 mg polysorbate to about 0.1 mg polysorbate per mg of the conjugate. When the polysorbate is polysorbate 20, the lyophilized composition preferably comprises about 0.02 mg polysorbate 20 per mg of the conjugate.

In order to prevent degradation of the active ingredients of the composition during freezing and drying, the inventive lyophilized composition further comprises a cryoprotectant, preferably an amorphous cryoprotectant. The term "cryoprotectant," as used herein, refers to an excipient that protects unstable molecules during freezing. Suitable cryoprotectants for use in the lyophilized composition are known to those skilled in the art, and include, for example, glycerol, dimethyl sulfoxide (DMSO), polyethylene glycol (PEG), dextran, glucose, trehalose, and sucrose. Most preferably, the cryoprotectant is sucrose. The cryoprotectant may be present in the inventive lyophilized composition in any suitable amount. The lyophilized composition desirably comprises about 0.5 mg to about 5 mg, for example, about 0.5 mg to about 2 mg of the cryoprotectant per mg of the conjugate, about 0.8 mg cryoprotectant per mg of the conjugate, about 2 mg cryoprotectant per mg of the conjugate, or about 4 mg cryoprotectant per mg of the conjugate. When the cryoprotectant is sucrose, the lyophilized composition preferably comprises about 0.5 mg to about 2 mg (e.g., about 1 mg) sucrose per mg of the conjugate.

The lyophilized composition can further contain a bulking agent, preferably a crystallizable bulking agent. Bulking agents typically are used in the art to provide structure and weight to the "cake" produced as a result of lyophilization. Any suitable bulking agent known in the art may be used in connection with the inventive lyophilized composition. Suitable bulking agents include, for example, mannitol, dextran, and glycine. The bulking agent used in the inventive composition most preferably is glycine. The lyophilized composition can contain any suitable amount of the bulking agent, but preferably the lyophilized composition comprises about 2 mg to about 20 mg of the bulking agent per mg of the conjugate, and preferably about 2 mg to about 10 mg bulking agent per mg of the conjugate, about 5 mg to about 10 mg bulking agent per mg of the conjugate, about 10 mg to about 15 mg bulking agent per mg of the conjugate, or about 15 mg to about 20 mg bulking agent per mg of the conjugate. When the bulking agent is glycine, the lyophilized composition preferably comprises about 3.8 mg glycine per mg of the conjugate.

Thus, in accordance with the invention, the contents of a lyophilized composition that is to be reconstituted to contain 5 mg/mL of conjugate (e.g., preferably a conjugate comprising huN901 chemically coupled to DM1) preferably comprises (i) about 0.3 mg sodium succinate buffer per mg of the conjugate, (ii) about 0.02 mg polysorbate 20 per mg of the conjugate, (iii) about 1 mg sucrose per mg of the conjugate, and (iv) about 3.8 mg glycine per mg of the conjugate. Once reconstituted with water, such a lyophilized composition preferably has a pH of about 5.5. Moreover, when the lyophilized composition is reconstituted with water, the descriptions of the relative concentrations of the excipients set forth above in connection with the liquid formulation are applicable to the aforesaid lyophilized composition.

Lyophilization methods are well known in the art and are described in, for example, Wang, W., Int. J. Pharm., 203, 1-60 (2000). For example, the inventive lyophilized composition can be produced using a lyophilization cycle comprising the following steps: (1) pre-cooling at a shelf temperature of 4° C. and ambient chamber pressure for 2.5 hours, (2) freezing at a shelf temperature of −50° C. and ambient chamber pressure for 14 hours, (3) glycine recrystallization at a shelf temperature of −20° C. and ambient chamber pressure for 6 hours, (4) re-freezing at a shelf temperature of −50° C. and ambient chamber pressure for 16 hours, (5) primary drying at a shelf temperature of −13° C. and 100 mTorr of pressure for 24 hours, (6) secondary drying at a shelf temperature of 24° C. and 100 mTorr of pressure for 10 hours, and (7) stopper phase at a shelf temperature of 24° C. and ambient chamber pressure. The lyophilized composition, however, is not limited to compositions produced by the above-described method. Indeed, any suitable lyophilization method can be used to produce the lyophilized composition, and it will be apparent to those skilled in the art that the chosen lyophilization parameters (e.g., drying times) will vary depending on a variety of factors, including the volume of the solution to be lyophilized.

In another embodiment, the present invention is directed to a kit for preparing an aqueous formulation, which kit contains both a first container containing a lyophilized powder and a second container containing an aqueous formulation comprising a reconstitution stabilizer. The concentration of the lyophilized powder in the solution, the solution volume which is charged into each container, and the capacity of the containers are all interrelated parameters which can be suitably modified, depending upon the desired concentration of active principle in the end dosage unit. Thus, these parameters may vary within wide ranges.

All patents, publications, and other references cited herein are expressly incorporated by reference in their entireties.

The present invention is further described by the following examples, which are illustrative of the process and should not be construed as limiting the invention. The process parameters given below can be adopted and adapted by the skilled person to suit the particular need.

EXAMPLE 1

This example shows the effect of the following formulation excipients on the visual appearance of formulated MAb-DM1 conjugate samples.

Samples of huN901-SPP-DM1 were set up at 1.0 mg/mL in 10 mM phosphate buffer pH 6.5 with 140 mM NaCl with each of the excipients listed below. Excipients were added directly to huN901-SPP-DM1 sample on a w/w % basis (weight of excipient/weight of solution). Immediately following addition of the excipient, the formulations were filtered, and appearance and particle counting tests were performed. Samples were then stored at 4° C. for the time of the study, and were tested again at 2 week and 1 month time points. For appearance, the samples were tested by examining at least 1.0 mL of solution against a white background for clarity and against a black background under white light for the presence or absence of visible particles. The results are reported as presence or absence of visible particles. Subvisible particles with the size above 5 μm were also measured with an HIAC particle counter calibrated to measure particle size between 2 and 100 μm.

Appearance:

| Excipient | Initial | 2 Weeks | 1 Month |
|---|---|---|---|
| 5% sucrose | Clear | Clear | Clear |
| 10% sucrose | Clear | Clear | Clear |
| 0.1% tween20 | Clear | Clear | Clear |
| 0.8% tween20 | Clear | Particles | Clear |
| 1% cyclodextrin | Clear | Clear | Clear |
| 1% dextrose | Clear | Clear | Particles |
| 5% glycerol | Clear | Clear | Particles |
| 2% PEG6000 | Clear | Clear | Particles |
| 5% mannitol | Clear | Particles | Particles |
| filtertered control* | Clear | Clear | Particles |

*filtered shortly before initial time point

Particle counting (counts>5 μm per mL):

| | Cummulative particle counts | | |
|---|---|---|---|
| Excipient | Initial | 2 Weeks | 1 Month |
| 5% sucrose | 94 | 120 | 84 |
| 10% sucrose | 68 | 14 | 58 |
| 0.1% Tween20 | 40 | 76 | 76 |
| 0.8% Tween20 | 86 | 120 | 120 |
| 1% Beta-Cyclodextrin | 8 | 4 | 10 |
| 1% Dextrose | 388 | 608 | 502 |
| 5% Glycerol | 4 | 32 | 42 |
| 2% PEG | 12 | 6 | 72 |
| 5% mannitol | 46 | 144 | 70 |
| filtered control | 222 | 284 | 720 |

Positive effects of sucrose, TWEEN-20™, beta-cyclodextrin, dextrose, glycerol, mannitol and polyethylene glycol (PEG) were observed.

EXAMPLE 2

This example shows the effect of amino acids on stability of huN901-SPP-DM1 with respect to conjugate aggregation.

Samples of huN901-SPP-DM1 were set up at 5.0 mg/mL in the following buffers and stored at 2-8 and 25° C. for 12 months. Conjugate aggregate content was tested with a chromatographic assay at 1, 3, 6 and 12-month time points.

(1) 10 mM sodium phosphate, 140 mM NaCl, pH 6.5.
(2) 10 mM sodium citrate, 135 mM NaCl, 0.01% polysorbate 20, pH 5.5.
(3) 10 mM sodium citrate, 130 mM histidine, 0.01% polysorbate 20, pH 5.5
(4) 10 mM sodium citrate, 110 mM glycine, 80 mM NaCl, 0.01% polysorbate 20, pH 5.5.

| | | 2-8° C. | | | | 25° C. | | | |
|---|---|---|---|---|---|---|---|---|---|
| Formulation | T0 | 1 mon | 3 mon | 6 mon | 12 mon | 1 mon | 3 mon | 6 mon | 12 mon |
| Composition 1 | 5.3 | 6.7 | 8.1 | 8.6 | 8.9 | 8.7 | 10.2 | 10.4 | 11.8 |
| Composition 2 | 4.5 | 5.0 | 5.4 | 5.6 | 5.5 | 5.8 | 6.6 | 7.2 | 8.2 |
| Composition 3 | 4.1 | 4.1 | 4.2 | 4.1 | 3.8 | 4.5 | 4.7 | 5.0 | 6.1 |
| Composition 4 | 4.2 | 4.5 | 4.8 | 4.9 | 4.9 | 5.2 | 5.8 | 6.2 | 7.3 |

Example 1 shows that histidine improves the formulation with regard to preventing conjugate aggregate formation. Glycine also has benefits.

EXAMPLE 3

This example shows the effect of histidine on the stability of huMy9-6-SPDB-DM4 conjugate in terms of conjugate aggregate.

The huMy9-6-SPDB-DM4 conjugate was formulated at 5.0 mg/mL in:

(1) 10 mM sodium citrate, 135 mM NaCl, pH 5.5
(2) 150 mM histidine/histidine chloride, pH 5.5

Samples were incubated at 2-8° C. and 25° C. for 6 months, after which they were tested for aggregate of conjugate by a chromatographic assay.

| Formulation | T0 | 2-8° C., 6 mon | 25° C., 6 mon |
|---|---|---|---|
| Composition 1 | 3.5 | 4.0 | 8.2 |
| Composition 2 | 3.2 | 3.2 | 7.1 |

The data shows the beneficial effects of histidine on preventing formation of aggregate.

EXAMPLE 4

This example shows the effect of buffering agent, sugar and amino acid on the stability of huC242-SPDB-DM4 with respect to conjugate aggregate.

Samples of huC242-SPDB-DM4 at 5.0 mg/mL in:
(1) 10 mM sodium citrate, 135 mM NaCl, pH 5.5
(2) 10 mM sodium citrate, 5% sucrose, 130 mM glycine, 0.1% polysorbate 80, pH 5.5
(3) 10 mM histidine/histidine chloride, 5% sucrose, 130 mM glycine, pH 5.5

Testing for conjugate monomer and aggregate contents were performed at $T_0$, and after 3 months of storage at 2-8° C. and 25° C.

| | Aggregate (%) | | |
|---|---|---|---|
| Formulation | $T_0$ | 2-8° C., 3 mon | 25° C., 3 mon |
| Composition 1 | 4.0 | 4.3 | 9.1 |
| Composition 2 | 3.2 | 3.7 | 5.9 |
| Composition 3 | 2.4 | 2.3 | 3.8 |

The data shows that sucrose and glycine, together in the above combination, improves the formulation with regards to protection against conjugate aggregation. The greatest improvement is observed when the sucrose and glycine combination is used with histidine.

EXAMPLE 5

This example shows the effect of various formulations containing sucrose with and without glycine on aggregate content of huN901-SPP-DM1 conjugate.

Samples of huN901-SPP-DM1 at 5.0 mg/mL concentration in each of the following liquid formulations were tested for monomer and aggregate contents.
(1) 10 mM sodium citrate, 135 mM NaCl, 0.01% polysorbate 20, pH 5.5
(2) 10 mM sodium citrate, 60 mM NaCl, 5% sucrose, pH 5.5
(3) 10 mM sodium citrate, 60 mM NaCl, 0.01% polysorbate 20, 5% sucrose, pH 5.5
(4) 10 mM sodium phosphate, 140 mM NaCl pH 6.5
(5) 10 mM sodium succinate, 0.25 M glycine, 0.01% polysorbate 20, 0.5% sucrose, pH 5.5

Samples stored at 25° C. were tested for aggregate contents at 3, 6 and 12 month time points.

| | Aggregate (%) | | |
|---|---|---|---|
| Formulation | 3 mon | 6 mon | 12 mon |
| Composition 1 | 6.7 | 7.3 | 8.2 |
| Composition 2 | 5.2 | 5.7 | 6.2 |
| Composition 3 | 5.6 | 5.4 | 6.5 |
| Composition 4 | 10.0 | 10.4 | 11.8 |
| Composition 5 | 4.4 | 4.7 | 4.4 |

In all cases formulations containing sucrose have lower aggregate content than ones without sucrose. The formulation containing glycine (composition 5) had the best stability in this example.

EXAMPLE 6

This example shows the effect of polysorbate 80 on particle formation induced by agitation. This stress condition (agitation) is expected to mimic stresses encountered during shipping and handling of liquid conjugate, as opposed to stresses encountered during static storage (which are addressed in Example 1).

Samples of huC242-SPDB-DM4 were set up at 1 mg/mL in the following buffers and placed in USP Type 1 glass vials (5 mL in a 10 mL vial) which were sealed with Flurotec® Stoppers. The vials were shaken for 48 hours at 100 rpm at room temperature, using a Lab-Line Orbital Shaker.
(1) 10 mM sodium citrate, 135 mM sodium chloride, pH 5.5
(2) 10 mM histidine, 5% sucrose, 130 mM glycine, pH 5.5
(3) 10 mM histidine, 5% sucrose, 130 mM glycine, 0.1% polysorbate 80, pH 5.5
(4) 10 mM histidine, 1% sucrose, 250 mM glycine, pH 5.5
(5) 10 mM histidine, 1% sucrose, 250 mM glycine, 0.1% polysorbate 80, pH 5.5
(6) 10 mM histidine, 280 mM glycine, pH 5.5
(7) 10 mM histidine, 280 mM glycine, 0.1% polysorbate 80, pH 5.5
(8) 10 mM histidine, 10% sucrose, pH 5.5
(9) 10 mM histidine, 10% sucrose, 0.1% polysorbate 80, pH 5.5

After shaking for 48 hours all vials were visually inspected. Those that contained polysorbate 80 (Compositions 3, 5, 7 and 9) remained clear, whereas all those that did not contain polysorbate 80 (1, 2, 4, 6 and 8) were cloudy. These data demonstrate the beneficial effect of polysorbate 80 in reducing particles due to agitation, such as might be encountered during shipping and handling of liquid conjugate.

We claim:

1. An immunoconjugate liquid formulation comprising:
   (i) an immunoconjugate, which is an antibody comprising one or more covalently linked hydrophobic cytotoxic drugs,
   (ii) 5-20 mM histidine,
   (iii) 100-300 mM glycine,
   (iv) 0.1-12% sucrose, and
   (v) 0.5-2% beta-cyclodextrin,
   wherein the pH of the formulation is 4.5 to 7.6.

2. The formulation of claim 1, wherein:
   said immunoconjugate is present in an amount of 0.5-20 mg/ml.

3. The formulation of claim 1, wherein:
   said immunoconjugate is present in an amount of 0.5-20 mg/ml,
   said histidine is present in an amount of 10-15 mM,
   said glycine is present in an amount of 130-250 mM, said sucrose is present in an amount of 5-10%, and
said beta-cyclodextrin is present in an amount of 0.5-1%.

4. The formulation of claim 3, wherein the formulation further comprises polysorbate 80 or polysorbate 20 in an amount of 0.005-0.2%.

5. The formulation of claim 4, wherein:
said sucrose is present in an amount of 5%,
said histidine is present in an amount of 10 mM, and
said glycine is present in an amount of 130 mM.

6. The formulation of claim 1, wherein the pH is from 5-7.

7. The formulation of claim 1, wherein the pH is from 5-6.

8. The formulation of claim 1, wherein said antibody is a humanized antibody selected from the group consisting of huMy 9-6, huN901, huC242, huB4, DS6, trastuzumab, bivatuzumab, sibrotuzumab, and rituximab.

9. The formulation of claim 1, wherein said antibody is huC242.

10. The formulation of claim 1, wherein said antibody is huN901.

11. The formulation of claim 1, wherein the cytotoxic drug is selected from the group consisting of a maytansinoid, a taxane, and a CC-1065.

12. The formulation of claim 10, wherein the cytotoxic drug is a maytansinoid.

13. The formulation of claim 11, wherein the cytotoxic drug is a maytansinoid.

14. The formulation of claim 11, wherein the cytotoxic drug is $N^{2'}$-deacetyl-$N^{2'}$-(3-mercapto-1-oxopropyl)-maytansine (DM1) or $N^{2'}$-deacetyl-$N^{2'}$-(4-methyl-4-mercapto-1-oxopentyl)-maytansine (DM4).

15. The formulation of claim 5, wherein:
said immunoconjugate is a humanized N901-DM1 immunoconjugate and is present in an amount of 0.5-10 mg/ml.

16. The formulation of claim 5, wherein:
said cytotoxic drug is $N^{2'}$-deacetyl-$N^{2'}$-(4-methyl-4-mercapto-1-oxopentyl)-maytansine(DM4) and said immunoconjugate is present in an amount of 0.5-10 mg/ml.

17. The formulation of claim 5, wherein:
said immunoconjugate is a humanized C242-DM4 immunoconjugate and is present in an amount of 0.5-10 mg/ml.

18. An immunoconjugate liquid formulation comprising:
(i) an immunoconjugate, which is an antibody comprising one or more covalently linked hydrophobic cytotoxic drugs,
(ii) 100-300 mM glycine,
(iii) 0.1-12% sucrose, and
(iv) 0.5-2% beta-cyclodextrin,
wherein the formulation is a buffered aqueous solution having a pH of 4.5 to 7.6.

19. The formulation of claim 18, wherein the formulation further comprises polysorbate 20 or polysorbate 80 in an amount of 0.005-1%.

20. The formulation of claim 18, wherein:
said immunoconjugate is present in an amount of 0.5-20 mg/ml.

21. The formulation of claim 18, wherein the pH is from 5-7.

22. The formulation of claim 18, wherein the pH is from 5-6.

23. The formulation of claim 18, wherein said antibody is a humanized antibody selected from the group consisting of huMy9-6, huN901, huC242, huB4, DS6, trastuzumab, bivatuzumab, sibrotuzumab, and rituximab.

24. The formulation of claims 23, wherein said antibody is huN901 or huC242.

25. The formulation of claim 18, wherein the cytotoxic drug is selected from the group consisting of a maytansinoid, a taxane, and a CC-1065.

26. The formulation of claim 18, wherein:
said immunoconjugate is a humanized N901-DM1 immunoconjugate and is present
in an amount of 0.5-10 mg/ml.

27. An immunoconjugate liquid formulation comprising:
(i) an immunoconjugate, which is an antibody comprising one or more covalently linked hydrophobic cytotoxic drugs,
(ii) 100-300 mM glycine,
(iii) 2-8% glycerol,
(iv) 0.5-2% beta-cyclodextrin, and
(v) 0.005-1.0% polysorbate 20 or polysorbate 80,
wherein the formulation is a buffered aqueous solution having a pH of 4.5-7.6.

28. The formulation of claim 27, wherein:
said immunoconjugate is present in an amount of 0.5-20 mg/ml,
said glycine is present in an amount of 130-250 mM,
said glycerol is present in an amount of 2-5%,
said beta-cyclodextrin is present in an amount of 0.5-1%, and
said is polysorbate 80 or polysorbate 20 is present in an amount of 0.005-0.2%.

29. The formulation of claim 27, wherein the pH is from 5-7.

30. The formulation of claim 27, wherein the pH is from 5-6.

31. The formulation of claim 27, wherein said antibody is a humanized antibody selected from the group consisting of huMy9-6, huN901, huC242, huB4, DS6, trastuzumab, bivatuzumab, sibrotuzumab, and rituximab.

32. The formulation of claim 27, wherein the cytotoxic drug is selected from the group consisting of a maytansinoid, a taxane, and a CC-1065.

33. The formulation of claim 27, wherein said cytotoxic drug is $N^{2'}$-deacetyl-$N^{2'}$-(3-mercapto-1-oxopropyl)-maytansine (DM1) or $N^{2'}$-deacetyl-$N^{2'}$-(4-methyl-4 -mercapto-1-oxopentyl)-maytansine (DM4).

34. An immunoconjugate liquid formulation comprising:
(i) an immunoconjugate, which is an antibody comprising one or more covalently linked hydrophobic cytotoxic drugs,
(ii) 2-8% mannitol,
(iii) 0.1-12% sucrose,
(iv) 0.5-2% beta-cyclodextrin, and
(v) 0.005-1.0% polysorbate 20 or polysorbate 80,
wherein the formulation is a buffered aqueous solution having a pH of 4.5-7.6.

35. The formulation of claim 34, wherein:
said immunoconjugate is present in an amount of 0.5-20 mg/ml,
said mannitol is present in and amount of 3-5%,
said sucrose is present in an amount of 5-10%, and
said is polysorbate 80 or polysorbate 20 is present in an amount of 0.005-0.2%.

36. The formulation of claim 34, wherein the pH is from 5-7.

37. The formulation of claim 34, wherein the pH is from 5-6.

38. The formulation of claim 34, wherein said antibody is a humanized antibody selected from the group consisting of huMy9-6, huN901, huC242, huB4, DS6, trastuzumab, bivatuzumab, sibrotuzumab, and rituximab.

39. The formulation of claim 34, wherein the cytotoxic drug is selected from the group consisting of a maytansinoid, a taxane, and a CC-1065.

40. The formulation of claim 18, wherein the buffered aqueous solution contains one or more of histidine, succinate, citrate, phosphate, and acetate.

41. The formulation of claim 40, wherein the buffered aqueous solution contains succinate.

42. The formulation of claim 40, wherein the buffered aqueous solution contains citrate.

43. The formulation of claim 18, wherein
said immunoconjugate is present in an amount of 0.5-20 mg/ml,
said glycine is present in an amount of 130-250 mM,
said sucrose is present in an amount of 5-10%, and
said beta-cyclodextrin is present in an amount of 0.5-1%.

44. The formulation of claim 43, wherein the formulation further comprises polysorbate 80 or polysorbate 20 in an amount of 0.005-0.2%.

45. The formulation of claim 18, wherein said cytotoxic drug is $N^{2'}$-deacetyl-$N^{2'}$-(3-mercapto-1-oxopropyl)-maytansine (DM1) or $N^{2'}$-deacetyl-$N^{2'}$-(4-methyl-4-mercapto-1-oxopentyl)-maytansine (DM4).

46. The formulation of claim 27, wherein the buffered aqueous solution contains one or more of histidine, succinate, citrate, phosphate, and acetate.

47. The formulation of claim 46, wherein the buffered aqueous solution contains succinate.

48. The formulation of claim 27, wherein:
said immunoconjugate is present in an amount of 0.5-20 mg/ml.

49. The formulation of claim 34, wherein the buffered aqueous solution contains one or more of histidine, succinate, citrate, phosphate, and acetate.

50. The formulation of claim 49, wherein the buffered aqueous solution contains succinate.

51. The formulation of claim 34, wherein:
said immunoconjugate is present in an amount of 0.5-20 mg/ml.

52. The formulation of claim 34, wherein said cytotoxic drug is $N^{2'}$-deacetyl-$N^{2'}$-(3-mercapto-1-oxopropyl)-maytansine (DM1) or $N^{2'}$-deacetyl-$N^{2'}$-(4-methyl-4-mercapto-1-oxopentyl)-maytansine (DM4).

* * * * *